(12) United States Patent
Brouillette et al.

(10) Patent No.: US 9,833,373 B2
(45) Date of Patent: Dec. 5, 2017

(54) MECHANICAL WAVE GENERATOR AND METHOD THEREOF

(75) Inventors: Martin Brouillette, Sherbrooke (CA);
Steven Dion, Sherbrooke (CA);
Louis-Philippe Riel, Sherbrooke (CA)

(73) Assignee: LES SOLUTIONS MÉDICALES SOUNDBITE INC., Saint-Laurent (CA)

(*) Notice: Subject to any disclaimer, the term of this patent is extended or adjusted under 35 U.S.C. 154(b) by 1319 days.

(21) Appl. No.: 13/819,575

(22) PCT Filed: Aug. 29, 2011

(86) PCT No.: PCT/IB2011/002701
§ 371 (c)(1),
(2), (4) Date: Feb. 27, 2013

(87) PCT Pub. No.: WO2012/025833
PCT Pub. Date: Mar. 1, 2012

(65) Prior Publication Data
US 2013/0158453 A1    Jun. 20, 2013

Related U.S. Application Data

(60) Provisional application No. 61/377,519, filed on Aug. 27, 2010.

(51) Int. Cl.
*A61H 1/00*     (2006.01)
*A61B 17/225*   (2006.01)
(Continued)

(52) U.S. Cl.
CPC ............. *A61H 1/00* (2013.01); *A61B 17/225* (2013.01); *B06B 3/00* (2013.01); *G10K 15/02* (2013.01); *G10K 15/043* (2013.01)

(58) Field of Classification Search
CPC .. B08B 3/12; B08B 7/026; B06B 3/00; B06B 1/0622; G10K 11/30; G10K 11/004; G01N 29/28
(Continued)

(56) References Cited

U.S. PATENT DOCUMENTS 3,942,531 A    3/1976  Hoff et al.
4,276,491 A    6/1981  Daniel
(Continued)

FOREIGN PATENT DOCUMENTS

JP    04-250356        9/1992
WO    WO2005018469    3/2005

OTHER PUBLICATIONS

International Preliminary Report on Patentability for PCT Application No. PCT/IB2011/002701, issued Mar. 5, 2013.
(Continued)

*Primary Examiner* — Bryan Gordon
(74) *Attorney, Agent, or Firm* — McDonnell Boehnen Hulbert & Berghoff LLP

(57) ABSTRACT

A wave generator has a wave emitter including an elongated dispersive waveguide and a source operatively connected to a first end of the waveguide. The source covers at least partially a surface area thereof. A signal generator is in operative connection with the transducer to create electrical signals. A computer is in operative connection with the signal generator to cause it to generate the electrical signals. A mechanical input wave is created by the source at the first end of the waveguide. The mechanical input wave is constructed independently of data related to a mechanical wave received from a source in the medium and taking into account the different predetermined propagation velocities of at least two component waves of the mechanical input wave so that they combine with each other at a second end
(Continued)

of the waveguide to form the desired mechanical output wave in the medium.

12 Claims, 12 Drawing Sheets

(51) Int. Cl.
    *B06B 3/00*     (2006.01)
    *G10K 15/02*     (2006.01)
    *G10K 15/04*     (2006.01)

(58) Field of Classification Search
    USPC .................................. 310/334, 344, 335, 336
    See application file for complete search history.

(56) References Cited

U.S. PATENT DOCUMENTS

| | | |
|---|---|---|
| 4,674,505 A | 6/1987 | Pauli et al. |
| 4,771,787 A | 9/1988 | Wurster et al. |
| 4,901,034 A | 2/1990 | Frank-Peter |
| 4,907,573 A * | 3/1990 | Nagasaki ............ A61B 17/2258 310/320 |
| 4,957,099 A | 9/1990 | Hassler |
| 5,048,527 A | 9/1991 | Okazaki |
| 5,064,265 A | 11/1991 | Khanarian et al. |
| 5,109,338 A | 4/1992 | Ermert et al. |
| 5,111,805 A | 5/1992 | Jaggy et al. |
| 5,116,343 A | 5/1992 | Ams et al. |
| 5,119,801 A | 6/1992 | Eizenhoefer et al. |
| 5,144,592 A | 9/1992 | Bonis |
| 5,165,388 A | 11/1992 | Hartinger |
| 5,174,280 A | 12/1992 | Gruenwald et al. |
| 5,193,527 A | 3/1993 | Schafer |
| 5,214,620 A | 5/1993 | Rattner |
| 5,247,924 A | 9/1993 | Suzuki et al. |
| 5,279,282 A | 1/1994 | Oppelt |
| 5,370,120 A | 12/1994 | Oppelt et al. |
| 5,481,153 A * | 1/1996 | Turner ................... G10K 11/24 310/327 |
| 5,509,417 A | 4/1996 | Dias et al. |
| 5,838,867 A | 11/1998 | Onishi et al. |
| 5,994,818 A | 11/1999 | Abramov et al. |
| 6,163,398 A | 12/2000 | Inagaki et al. |
| 6,948,843 B2 | 9/2005 | Laugharn et al. |
| 7,264,597 B2 | 9/2007 | Cathignol |
| 2002/0040199 A1 | 4/2002 | Klopotek |
| 2002/0108631 A1 * | 8/2002 | Madanshetty ............ B08B 3/12 134/1 |
| 2002/0161301 A1 * | 10/2002 | Venkataramani ...... G10K 11/02 600/459 |
| 2003/0199857 A1 | 10/2003 | Eizenhofer |
| 2004/0030227 A1 | 2/2004 | Littrup et al. |
| 2005/0131289 A1 | 6/2005 | Aharoni et al. |
| 2006/0029525 A1 | 2/2006 | Laugharn et al. |
| 2008/0009885 A1 | 1/2008 | Del Giglio |
| 2008/0084604 A1 | 4/2008 | Barker et al. |
| 2008/0146970 A1 | 6/2008 | Litman et al. |
| 2009/0093724 A1 | 4/2009 | Pernot et al. |
| 2010/0000074 A1 * | 1/2010 | Smith ............ A61B 17/320092 29/594 |

OTHER PUBLICATIONS

International Search Report for PCT Application No. PCT/IB2011/002701, mailed Mar. 12, 2012.

Written Opinion for PCT Application No. PCT/IB2011/002701, mailed Mar. 12, 2012.

Montaldo, G., et al., "Generation of very high pressure pulses with 1-bit time reversal in a solid waveguide," J. Acoust. Soc. Am., vol. 110 (6), pp. 2849-2857, Dec. 2001.

Meykens, K., et al., "Dispersion in acoustic waveguides—A teaching laboratory experiment," Am. J. Phys., vol. 67 (5), pp. 400-406, May 1999.

Puckett, A.D., et al., "A time reversal mirror in a solid circular waveguide using a single, time-reversal element," ARLO, vol. 4 (2), pp. 31-36, Apr. 2003.

Roux, P., et al., "Time-reversal in an ultrasonic waveguide," App. Phys. Lett., vol. 70 (14), pp. 1811-1813, Apr. 1997.

Supplementary International Search Report of PCT/IB2011/002701 mailed on Nov. 9, 2012.

Birer et al., Compact Self Focusing Piezoelectric Generator Using Electrically Pre-Stressed Transducer for Strong Sound Pulses in Therapy, IEEE Ultrasonics Symposium, 2002, pp. 1281-1284.

* cited by examiner

MECHANICAL WAVE GENERATOR AND METHOD THEREOF

CROSS REFERENCE

The present application is a U.S National Phase Aplication pursuant to 35 U.S.C. §371 of International Application No. PCT/IB2011/002701, filed Aug. 29, 2011, which claims priority to U.S. Provisional Patent Application No. 61/377,519, entitled 'Mechanical Wave Generator and Method Thereof', filed Aug. 27, 2010. The entire disclosure contents of these applications are herewith incorporated by reference into the present application.

TECHNICAL FIELD

This invention relates to devices for generating mechanical waves and methods thereof.

BACKGROUND

A "mechanical wave" is a disturbance that propagates through a medium due to the restoring forces it produces upon deformation of the medium. Solids, liquids, gases, and gels are examples of media through which a mechanical wave may travel.

If desired, the energy of a mechanical wave can be exploited to deform and potentially fracture an object placed in the medium. For example, high intensity compression pulses (i.e., a brief wave of great amplitude) can be sent in the body of a patient to break a kidney stone apart.

One protocol for kidney stone destruction consists of emitting a compression pulse having a sufficient amount of energy for traveling through the body, reaching the stone, and potentially rupturing the kidney stone upon contact. Machines used in medical kidney stone destruction are known in the art as lithotripters. The external lithotripters send externally-applied, focused, high-intensity compression pulses toward the kidney stone. As the high intensity compression pulses travel through the body of the patient, non-linear effects eventually deform these pulses into shockwaves. When a shockwave encounters a non-homogeneity such as the kidney stone, a relatively large amount of energy is transferred from the shockwave to the kidney stone in a (relatively) very short period of time. Ideally, this energy transfer is sufficient to break enough of the bonds between the stone particles to destroy the stone. With external lithotripters, the location of the kidney stone within the body of the patient must be known in order to direct the high-intensity compression pulses toward the kidney stone.

Despite their widespread use, conventional lithotripters are cumbersome apparatuses. First, they have the drawbacks of potentially damaging tissue adjacent to the kidney stone and producing large kidney stone fragments. Second, they have a limited focal length. Occasionally, conventional machines even fail to fragment the hardest kidney stones. Finally, conventional lithotripters often require the inclusion of apparatuses such as fluoroscopy (x-ray) or ultrasound machines for locating the kidney stone.

Montaldo et al. '*Generation of very high pressure pulses with 1-bit time reversal in a solid waveguide*', J. Acoust. Soc. Am. 110(6), December 2001 have developed a way to focus high amplitude pressure pluses at predetermined locations in a fluid. The system of Montaldo et al. works according to the time-reversal mirror concept, which exploits the temporal reversibility (or reciprocity) of the wave equation of motion. Reciprocity says that if the wave equation has a solution, the time reversal (using a negative time) of that solution is also a solution of the wave equation.

The system S proposed by Montaldo et al., shown in FIG. 1, is composed of seven small independent bi-directional piezoelectric transducers T glued to one end of an aluminum bar (waveguide), which acts as a reverberative cavity RC. The transducers T can both emit and receive mechanical waves. The walls of the reverberative cavity RC are in contact with the air while the end of the reverberative cavity RC distal to the transducers T lies in water. In their experiment, Montaldo et al. use a source placed in the water to emit a pressure pulse toward the reverberative cavity RC. The pressure pulse is, after propagation through the reverberative cavity RC, recorded by each of the transducers T. As it travels through the reverberative cavity RC, the pressure pulse P undergoes some deformation due to reverberations R inside the reverberative cavity RC, as described below. The transducers T convert the recorded pressure pulse into an electric signal. The signal of each transducer T is then time reversed and processed to excite the same transducer T. The mechanical waves produced by each transducer T propagate through the reverberative cavity RC, by reverberations R, toward the other end of the reverberative cavity RC, and emerge at that end thereof to produce a focused pressure pulse W2 (shown in FIG. 2) at the location of the source.

As shown in FIG. 2, when a mechanical wave W1 created by one or more of the transducers T is propagated inside the cavity RC, reverberations R at the wall of the cavity RC redirected it to the core of the cavity RC. The reverberations R are a consequence of the difference of acoustic impedance between the reverberative cavity RC and the surrounding air. Since the wall reverberations R are with almost no energy loss, the mechanical wave W1 can travel inside the reverberative cavity RC without undergoing major attenuation. Each reverberation R creates the illusion of having originated from a virtual transducer VT. The assembly of these virtual transducers VT is perceived by an observer at a focal point FP as a source of great dimension, although only a limited number of real transducers RT is used.

As a consequence, the technology proposed by Montaldo et al. uses a limited number of low-power transducers to temporally and spatially concentrate trains of low amplitude waves in order to obtain a high amplitude and short-lasting focused wave. The spatial focalisation is made possible by the reverberating nature of the cavity while the temporal compression is made possible by the time reversal operation. Montaldo et al. sends the pulses at predetermined locations which correspond to locations where a source was originally positioned.

Montaldo et al.'s device reaches some limits, especially when applied to lithotripsy. A simple calculation can show that their proposed device is not capable of reaching focal distances compatible with applications where the target is typically remote from the wave emitting device. Further, to reach typical focal distances required for kidney stones destruction in human subjects, one would need to construct a device having an unrealistic number of transducers or else have the reverberative cavity of a cumbersome length or diameter. A device of such a size is far from Montaldo et al.'s main object which was to present a simple and compact alternative to current commercial lithotripters, and this probably explains why there is no evidence of the construction of such a device in literature.

Thus, in summary, in terms of the use of wave generators of high intensity acoustic pulses with possible applications in lithotripsy, it is believed that conventional technology has reached its limits in what it will allow, and the disadvantages noted above remain. While the wave generator proposed by Montaldo et al. may assist in ameliorating the situation, room for improvement would nonetheless still exist.

SUMMARY

It is an object of the present invention to ameliorate at least some of the inconveniences mentioned above. It is also an object of the present invention to provide an improved wave generator that generates mechanical waves by, amongst other things, exploiting the dispersive properties of a waveguide. It is also an object of the invention to provide an improved wave generator that generates high intensity pulses from low power components. It is also an object of the invention to provide an improved wave generator that generates one or more mechanical waves as desired and chosen by a user, independently of an emitting source in the environing medium of the wave generator.

In a first aspect, the wave generator of the present invention includes an elongated dispersive waveguide and a source covering at least partially one end of the waveguide. The source is programmable to generate one or more mechanical waves in the dispersive waveguide. Because the waveguide is dispersive, a mechanical wave gets typically distorted as it travels through the waveguide. When reaching the end of the waveguide distal to the source, at least components waves composing the mechanical waves recombine due to the dispersive effects to form a desired wave that is emitted in the medium in contact with the end of the waveguide distal to the source. Because the source is programmable and at least some of the dispersive properties of the waveguide can be predetermined, the mechanical wave generated in the dispersive waveguide can be determined so as to form, when recombined, an emitted wave as chosen by the user. The device of the present invention works by beneficially exploiting dispersion. Dispersion is an intrinsic property of the geometry and composition of the waveguide.

Any waveform can be decomposed into a finite sum of component waves. The components waves each include a function in time and a function in space. Each component wave has an associated frequency, magnitude and phase in time and an associated deformation field in space. A specific shape of the deformation field corresponds to a mode of the waveguide. Thus for the purposes of this application, we will consider that a component wave has an associated frequency, an associated magnitude, an associated phase and an associated mode of the waveguide. As a consequence, two component waves can have a same frequency and excite different modes. Two component waves can also have different frequencies and excite a same mode. Two component waves can also have different frequencies and excite different modes. For the purpose of this application, we will consider that the modes are longitudinal modes propagating in a longitudinal axis of an elongated waveguide. For a mechanical wave traveling in the waveguide, a component wave has an associated propagation velocity. When the propagation velocity in the waveguide depends on the frequency and the mode of the component wave, the waveguide is qualified as 'dispersive'. Thus, a dispersive waveguide compels a relative phase difference of the component waves of a mechanical wave, which transforms a pulse (ordered phase component waves) into an oscillation train having a lower amplitude and a longer temporal span (rearranged component waves).

An example of dispersion in a dispersive waveguide is shown in FIGS. 3A-3F. It is contemplated that the dispersion would be similar in a dispersive medium other than a waveguide. A pulse P (characterized by its amplitude A distribution in function of time t, as shown in FIG. 3A) has a plurality of component waves (shown in FIG. 3B), each of them being characterized by their unique frequency f, their associated phase $\phi$ (or relative phase) (shown FIG. 3C), their magnitude M (shown in FIG. 3B) and their mode. The pulse P becomes a dispersed wave DW (characterized by its amplitude A distribution in function of time t, as shown in FIG. 3D) after propagation in the dispersive waveguide. The dispersed wave DW has the same component waves (shown in FIG. 3E) characterized by the same frequencies f, the same magnitude M (shown in FIG. 3E) but different associated phases $\phi$ (shown in FIG. 3F). As shown in FIGS. 3C and 3F, the dispersive properties of the waveguide have introduced a phase shift between the component waves traveling through the dispersive waveguide. It is assumed that the waveguide is dispersive with no attenuation, as illustrated in FIGS. 3B and 3E where a maximum magnitude $M_1$ is the same for in FIGS. 3B and 3E. It is contemplated that some attenuation could be present.

The inventors have realized that, when the dispersive properties of a waveguide are known, it is possible to program a source so as to generate a mechanical wave where the component waves of the mechanical wave have associated phases such that, once phase shift is introduced by the dispersive waveguide, the mechanical wave recombines at the other end of the waveguide into the desired mechanical wave. The wave generator of the present invention works according to this principle, by exploiting the dispersive properties of a waveguide to generate desired mechanical waves. Since the emitted mechanical waves are chosen by the user, in some cases, the wave generator can also be used as a 'passive amplifier' to generate high amplitude acoustic pulses.

Contrary to the present device, the wave generator of Montaldo et al. exploits reverberations, and not dispersion, to amplify mechanical waves. However, it should be noted that Montaldo et al. in '*Generation of very high pressure pulses with 1-bit time reversal in a solid waveguide*', J. Acoust. Soc. Am. 110(6), December 2001, refer wrongly to reverberation as a 'dispersion'. Indeed, similarities between this device and the one previously described by their colleagues Roux et al. in '*Time-reversal in an ultrasonic waveguide*', Applied Physics Letters 70(14), February 1997, show that the amplification is attributable to reverberations rather than to dispersion. It may be that some actual dispersion does occur, but as Montaldo et al. noted, this dispersion is compensated for (as opposed to being exploited by) the time reversal operation. Thus, Montaldo et al. rely on reverberation and not dispersion to operate their device.

To generate the desired mechanical waves, the dispersive properties of the waveguide are predetermined. Knowing the dispersive properties consists in knowing the relationships between component waves and propagation velocities in the waveguide. A unique calibration step is sufficient to determine the dispersive properties. The calibration step can be done experimentally or analytically. In one example, the finite element method is used to determine the dispersion relationships. In another example, a hydrophone can be used to experimentally determine the dispersive properties.

Initial calibration of the wave generator is done independently of an emitting source present in the medium. Montaldo et al., however, rely on an emitting source to calibrate initially their device. Further, the wave generator of the present invention uses the same calibration whatever the focal point is, whereas Montaldo et al. require a moving emitting source to calibrate different focal points. In addition, the present device can generate selected desired mechanical output waves that are designed according to the application the user intends to use the mechanical waves for, contrary to Montaldo et al. which device only generates mechanical output waves according the emitting source.

Furthermore, because the present invention uses a source (e.g. a single transducer) covering totally or partially an end of the waveguide, the mechanical waves generated can be one dimensional. The device of Montaldo et al. has instead a plurality of bi-directional transducers covering only partially the end of the reverberative cavity RC (as can be seen in FIG. 1) and this arrangement generates multi-dimensional waves. Opposite to what Montaldo et al. implies, a one-dimensional source (e.g. single transducer) can as much exploit dispersion as a tridimensional source (e.g. plurality of transducers), and that even when the wavelength of the mechanical wave is small compared to the waveguide diameter. For example, Puckett et al. in '*A time- reversal mirror in a solid circular waveguide using a single, time-reversal element*', ARLO 4(2), April 2003, cleans the echoes present in a buffer rod placed between a target medium and a transducer by using the temporal reverse mirror method in order to cancel the undesired effects of dispersion. Thus, since it is possible to eliminate the phase difference of a signal caused by dispersion with only one transducer covering a whole end of the buffer rod, it is as much possible to efficiently exploit that dispersion in order to increase tenfold a one-dimensional source power.

Because the present wave generator can use a one-dimensional source, the wave generator can generate planar waves, which can propagate at relatively long distances away from the emitting end of the waveguide. In comparison, the device of Montaldo et al. generates pulses focused at locations relatively close to the emitting end of the waveguide.

The present wave generator can generate planar waves which excite a single mode. In some cases, the wave generator can excite solely the fundamental (first) mode of the waveguide. Although the present wave generator may be capable of exciting multiple modes, the present wave generator does not require to excite more than one mode.

Thus, in a first aspect, as embodied and broadly described herein, the present invention provides a wave generator for emitting a desired mechanical output wave into a medium. The generator comprises a wave emitter including an elongated dispersive waveguide having a first end and a second end. When in operation the second end is at least partially in contact with the medium. A source is operatively connected to the first end of the dispersive waveguide covering at least partially a surface area of the first end. The source is operative to generate a mechanical input wave in the dispersive waveguide based on electrical signals input to the source. A signal generator is in operative connection with the source. The signal generator is operative to create the electrical signals converted by the source into the mechanical input wave in the dispersive waveguide. A computer is in operative connection with the signal generator, the computer having a processor and a machine-readable storage medium. The machine-readable storage medium contains instructions that when executed by the processor cause the signal generator to create electrical signals converted by the source into the mechanical input wave. The mechanical input wave has at least two component waves. Each of at least two of the component waves has a unique predetermined propagation velocity through the dispersive waveguide. The mechanical input wave is constructed (i) independently of data related to a mechanical wave received from a source in the medium and (ii) taking into account the different predetermined propagation velocities of the at least two component waves so that the at least two component waves combine at least partially with each other at the second end of the dispersive waveguide to form the desired mechanical output wave emitted into the medium.

In some embodiments, the desired mechanical output wave has an amplitude greater than an amplitude of the mechanical input wave, and in some other embodiments the desired mechanical output wave is temporally compressed relative to the mechanical input wave. A constructive recombination can occur when slower component waves of the mechanical input wave are sent in the dispersive waveguide before faster component waves, at time intervals that compensate for the relative phase shift introduced by the dispersive waveguide. The slower and the faster component waves interact with each other at a specific location in the dispersive waveguide. When the interaction is constructive (i.e. when the components waves have both a positive magnitude), the resultant mechanical wave has an increased amplitude. It is contemplated that, in other embodiments, a destructive recombination (or another type of combination) of the two component waves) could be preferred to create specific output mechanical waves. Resulting to the interaction, one can create a desired mechanical output wave that is temporally compressed after traveling through the dispersive waveguide.

By programming the source so as to have slower component waves sent before faster component waves, the constructive interaction can be used for the generation of high intensity pulses. Whereas dispersion is typically avoided in wave-guiding devices, the inventors have found a way to use and exploit a dispersive waveguide as a wave amplifier (or wave compressor). As a consequence, in the device proposed by the inventors, it is no longer required to have high energy components to generate high intensity mechanical waves. For example, a low voltage transducer with large frequency domain is sufficient to create high intensity pulses. In some cases, it is even possible to create a high intensity pulse having an amplitude over ten times larger than that of a train of low intensity waves input into the dispersive waveguide.

In some embodiments, the at least two component waves have an associated frequency and an associated mode of the waveguide. The at least two component waves have different associated frequencies. The at least two component waves have a same associated mode.

In some embodiments, the same associated mode is a single mode of the waveguide.

In some embodiments, the single mode is a fundamental longitudinal mode of the waveguide.

In other embodiments, the at least two component waves have different associated modes. The at least two component waves have a same associated frequency.

In some embodiments, the source is a transducer.

In some embodiments, the source has a frequency bandwidth. The at least two component waves have each an associated frequency. The associated frequencies of the at least two component waves are within the frequency bandwidth of the source. a frequency bandwidth of the source, an attenuation coefficient of the dispersive waveguide is such that the wave emitter has a positive gain. To ensure that the source generates mechanical waves that have frequency components in the dispersive region of the waveguide, it is preferable to have the frequency bandwidth of the source at least partially within the dispersive region of the waveguide.

In some embodiments, the source covers at least entirely the surface area of the first end of the dispersive waveguide. When the source covers entirely the surface area of the first end of the dispersive waveguide, little reverberation interfere with the mechanical wave traveling through the dispersive waveguide, and the output mechanical wave corresponds to the desired mechanical wave as computed from the dispersion relations. While Montaldo et al. rely on reverberations to amplify the mechanical waves, reverberations are not exploited for the operation of the wave generator of the present invention.

In some embodiments, the dispersive waveguide has a constant cross-section. In applications where the dispersive waveguide has a constant cross-section, reverberations are limited.

In some embodiments, the wave generator further comprises at least one of an acoustic impedance coupler and an acoustic lens operatively connected to the second end of the dispersive waveguide. To optimize energy transmission of the output mechanical wave between the dispersive waveguide and the medium, the acoustic impedance coupler can be positioned between the wave emitter and the medium. The acoustic impedance coupler is used to match the acoustic impedance of the dispersive waveguide with the acoustic impedance of the medium, thereby minimizing reflection between the two. In some embodiments, the acoustic impedance coupler includes at least one layer. The at least one layer has an acoustic impedance intermediate to an acoustic impedance of the dispersive waveguide and to an acoustic impedance of the medium. The at least one layer is chosen as a function of its acoustic impedance so as to maximize energy transmission of the desired mechanical output wave between the second end of the dispersive waveguide and the medium. An acoustic lens can be used to geometrically focus the desired mechanical output wave. In some applications where a target is at a known location and it is desired to generate spatially concentrated mechanical waves, the desired mechanical output wave can be further geometrically focused.

In some embodiments, within a frequency bandwidth of the source, an attenuation coefficient of the dispersive waveguide is such that the wave emitter has a positive gain. For some applications, the dispersive waveguide is chosen to have a low attenuation coefficient at frequencies of interest in order to maximize gain. The frequencies of interest are the frequencies comprised within the source's frequency bandwidth which are also frequencies for which the waveguide is dispersive. The attenuation coefficient describes the extent to which the intensity of a wave is reduced as it passes through a specific material (i.e., the waveguide) due to internal friction and heat losses.

In some embodiments, the dispersive waveguide is one of the group consisting of a metal and a ceramic. Metals and ceramic have preferably a low attenuation coefficient of the frequencies of interest. A material for the dispersive waveguide is preferably chosen to have a high Poisson coefficient, low attenuation coefficient, and low propagation velocity. An acoustic impedance is preferably as close as possible to that of the source and the medium in order to maximize transmission of energy.

In some embodiments, an aspect ratio of the dispersive waveguide is at least 10. For a cylindrical waveguide, the aspect ratio could preferably be approximately be between 10 and 1000. A somewhat large aspect ratio enhances amplification in embodiments where high intensity mechanical waves are desired. The longer the rod, the more amplification can be obtained. The waveguide has a length that preferably allows a significant amplification gain and allows the user to identify the signal from noise at the calibration step. A somewhat low aspect ratio has for consequence that the waveguide may be weakly dispersive.

In some embodiments, the desired mechanical output wave is generally planar. In applications where the source covers most or more of the first end of the dispersive waveguide, the desired mechanical output wave is generally planar (one dimensional).

In some embodiments, the desired mechanical output wave is unfocused. In applications where planar mechanical waves are generated, the desired mechanical output wave is unfocused.

In some embodiments, the desired mechanical output wave is focused. In one example, the desired mechanical output wave is geometrically focused. In another example, diffraction effects at the second end of the dispersive waveguide are used to focus energy at a predetermined spatial location within the medium.

In other embodiments, the dispersive waveguide is curved along its length at least in part between the first end and the second end.

In yet other embodiment, the dispersive waveguide has a radius of curvature at least an order of magnitude of wavelengths of the at least two component waves.

In some embodiments, the dispersive waveguide is flexible. By 'flexible' it should be understood a material capable of being (relatively easily—during the intended application of the device) bent or curved, but not necessarily foldable. A waveguide that is flexible can be used for space saving or when reaching places with restricted access. In some cases, the procedure requires that the mechanical waves be emitted in the vicinity of a target and/or for increasing the transmission of energy. Thus, a flexible waveguide might allow for the positioning of the wave emitter right in front of the target, even when the target may be difficult to access.

In some embodiments, the wave generator further comprises an amplifier operatively connected to the signal generator. The amplifier is operative to modify an amplitude of at least a portion of the electric signals input to the source. In one example, the amplifier is used to saturate the electric signals input to the source.

In some embodiments, the source is a bi-directional transducer and is further operative to generate electrical signals from a reverse direction mechanical wave. The reverse direction mechanical wave propagates through the waveguide from the second end toward the first end of the waveguide. The wave generator further comprises a switch in operative connection with the bi-directional transducer and the coupler. The switch separates input electric signals from output electric signals to the bi-directional transducer. A digitizer is in operative connection with the switch and with the computer. The digitizer is operative to digitize the output electrical signals. In some applications, for example where the location of a target is to be known, it is possible to use a bi-directional transducer for sensing (in addition to emitting mechanical waves) perturbations of the medium (or environment). When a mechanical wave is sent into a medium having a non-homogeneity (such as a kidney stone in the body), the non-homogeneity reflects this wave. A wave emitter having reception capability is able to detect that reflected wave and, and with the help of the computer, a position of the non-homogeneity can be calculated.

In another aspect, a wave generator for emitting a desired mechanical output wave into a medium is provided. The wave generator comprises a wave emitter including an elongated dispersive waveguide having a first end and a second end. When in operation the second end is at least partially in contact with the medium. A source is operatively connected to the first end of the dispersive waveguide and covers at least partially a surface area of the first end. The source is operative to generate a mechanical input wave in the dispersive waveguide based on electrical signals input to the source. A signal generator is in operative connection with the source. The signal generator is operative to create the electrical signals convertible by the source into the mechanical input wave in the dispersive waveguide. A computer is in operative connection with the signal generator. The computer has a processor and a machine-readable storage medium. The machine-readable storage medium contains instructions that when executed by the processor cause the signal generator to create electrical signals convertible by the source into the mechanical input wave. The mechanical input wave has at least two component waves. Each of the at least two component wave has a unique associated predetermined propagation velocity through the dispersive waveguide. The at least two component waves have a first relative phase shift. The first relative phase shift is determined so as to be become, at the second end of the dispersive waveguide, a second relative phase shift different from the first relative phase shift owing to the predetermined propagation velocities through the dispersive waveguide of the at least two component waves.

In some embodiments, the mechanical input wave has a first amplitude. The desired mechanical output wave has a second amplitude. The second relative phase shift is determined so that the second amplitude is greater than the first amplitude.

In some embodiments, the at least two component waves have an associated frequency and an associated mode of the waveguide. The at least two component waves have different associated frequencies, and the at least two component waves have a same associated mode. In yet other embodiments, the at least two component waves have different associated modes, and the at least two component waves have a same associated frequency.

In yet another aspect, a method of emitting a desired mechanical output wave into a medium is provided. The method comprises providing an elongated dispersive waveguide having a first end and a second end. The second end is at least partially in contact with the medium. The method comprises determining the desired mechanical output wave; determining a mechanical input wave. The mechanical output wave has at least two component waves. Each of the at least two component waves having a unique associated predetermined propagation velocity through the dispersive waveguide. At least two of the component waves have different predetermined propagation velocities through the dispersive waveguide. The mechanical input wave when inputted at the first end of the dispersive waveguide and once having propagated through the dispersive waveguide combine at least partially at the second end of the dispersive waveguide to form the desired mechanical output wave. The mechanical input wave is constructed (i) independently of data related to a mechanical wave received from a source in the medium and (ii) taking into account the different predetermined propagation velocities of the at least two component waves. The method comprises generating the mechanical input wave at the first end of the dispersive waveguide; allowing the mechanical input wave to propagate through the dispersive waveguide toward the second end; combining the mechanical input wave to form the desired mechanical output wave at the second end of the dispersive waveguide owing to differences in the predetermined propagation velocities of the at least two component waves; and emitting the desired mechanical output wave into the medium at the second end of the dispersive waveguide.

In an additional aspect, the method comprises combining the mechanical input wave having a first duration in time to form the desired mechanical output wave having a second duration in time includes shortening the first duration in time into the second duration in time.

In a further aspect, the method comprises combining the mechanical input wave to form the desired mechanical output wave includes combining the mechanical input wave having a first amplitude to form the desired mechanical output wave having a second amplitude. The second amplitude is greater than the first amplitude.

In an additional aspect, the at least two component waves have an associated frequency and an associated mode of the waveguide. The at least two component waves have different associated frequencies. The at least two component waves have a same associated mode.

In a further aspect, the same associated mode is a single mode of the waveguide.

In some embodiments, the single mode is a fundamental longitudinal mode of the waveguide.

In an additional aspect, the at least two component waves have each an associated frequency and an associated mode of the waveguide. The at least two component waves have different associated modes. The at least two component waves have a same associated frequency.

In an additional aspect, the source is a transducer.

In a further aspect, the source has a frequency bandwidth. The at least two component waves have each an associated frequency. The associated frequencies of the at least two component waves are within the frequency bandwidth of the source.

In an additional aspect, the source covers at least an entirety of the surface area of the first end of the dispersive waveguide.

In a further aspect, the dispersive waveguide has a constant cross-section.

In an additional aspect, the method further comprises emitting the desired mechanical output wave in at least one of an acoustic impedance coupler and an acoustic lens before emitting the desired mechanical output wave in the medium.

In a further aspect, the acoustic impedance coupler includes at least one layer before emitting the desired mechanical output wave in the medium. The at least one layer has an acoustic impedance intermediate to an acoustic impedance of the dispersive waveguide and to an acoustic impedance of the medium. The at least one layer is arranged as a function of its acoustic impedance so as to maximize energy transmission of the desired mechanical output wave between the second end of the dispersive waveguide and the medium.

In an additional aspect, within a frequency bandwidth of the source, an attenuation coefficient of the dispersive waveguide is such that the wave emitter has a positive gain.

In a further aspect, the dispersive waveguide is one selected from the group consisting of a metal and a ceramic.

In an additional aspect, an aspect ratio of the dispersive waveguide is at least 10.

In an additional aspect, emitting the desired mechanical output wave into the medium includes emitting the desired mechanical output wave as a generally planar wave.

In a further aspect, emitting the desired mechanical output wave into the medium includes emitting the desired mechanical output wave unfocused in the medium.

In an additional aspect, emitting the desired mechanical output wave into the medium includes emitting the desired mechanical output wave focused in the medium.

In a further aspect, the dispersive waveguide is curved along its length at least in part between the first end and the second end.

In yet a further aspect, the dispersive waveguide has a radius of curvature at least an order of magnitude of wavelengths of the at least two component waves.

In an additional aspect, the dispersive waveguide is flexible.

In a further aspect, the method further comprises determining a cut-off amplitude; saturating the input electrical signal to the cut-off amplitude to become a saturated signal; and amplifying at least a portion of the saturated signal, before inputting the input electrical signal to the source.

In an additional aspect, generating the mechanical input wave at the first end of the dispersive waveguide includes: generating an input electrical signal corresponding to the mechanical input wave; and inputting the input electrical signal to a source disposed at the first end of the dispersive waveguide. The source transforms the input signal into the mechanical input wave.

A method of emitting a desired mechanical output wave into a medium is also provided. The method comprises providing an elongated dispersive waveguide having a first end and a second end. The second end is at least partially in contact with the medium. The method comprises determining the desired mechanical output wave; and determining a mechanical input wave. The mechanical input wave has at least two component waves. Each of at least two of the component waves has a unique predetermined propagation velocity through the dispersive waveguide. The at least two component waves having a first relative phase shift. The first relative phase shift is determined so as to be become, at the second end of the dispersive waveguide, a second relative phase shift different from the first relative phase shift owing to the predetermined propagation velocities through the dispersive waveguide of the at least two component waves. The method comprises generating the mechanical input wave at the first end of the dispersive waveguide; allowing the mechanical input wave to propagate through the dispersive waveguide toward the second end; combining the mechanical input wave to form the desired mechanical output wave at the second end of the dispersive waveguide owing to differences in the predetermined propagation velocities of the at least two component waves; and emitting the desired mechanical output wave into the medium at the second end of the dispersive waveguide.

For the purpose of this application, the term "wave", as used herein, includes all mechanical waves, i.e., waves that propagate through a medium due to restoring forces they produce upon deformation of the medium. The term "component waves" refers to functions of space and time on which a mechanical wave can be decomposed. The term "medium", as used herein, refers to any substance (e.g. gas, liquid, solid, gel, non-biological or biological material) that allows for the propagation of a mechanical wave through it. The term "waveguide", as used herein, refers to a structure that conveys mechanical waves between its endpoints. The term "shockwave", as used herein, refers to a region of abrupt change of pressure that moves a wave front at a relatively rapid velocity through a medium. The term "acoustic", as used herein, refers to mechanical waves in gases, liquids, and solids at frequencies in the range of the sound, ultrasound and infrasound. The term "dispersion", as used herein, refers to a physical property of a waveguide by which component waves have different propagation velocities through that waveguide. The term "source" refers to any element capable of generating a generally planar longitudinal mechanical wave.

Embodiments of the present invention each have at least one of the above-mentioned objects and/or aspects, but do not necessarily have all of them. It should be understood that some aspects of the present invention that have resulted from attempting to attain the above-mentioned objects may not satisfy these objects and/or may satisfy other objects not specifically recited herein.

Additional and/or alternative features, aspects, and advantages of embodiments of the present invention will become apparent from the following description, the accompanying drawings, and the appended claims.

BRIEF DESCRIPTION OF THE DRAWINGS

For a better understanding of the present invention, as well as other aspects and further features thereof, reference is made to the following description which is to be used in conjunction with the accompanying drawings, where.

DETAILED DESCRIPTION

Figure 1:
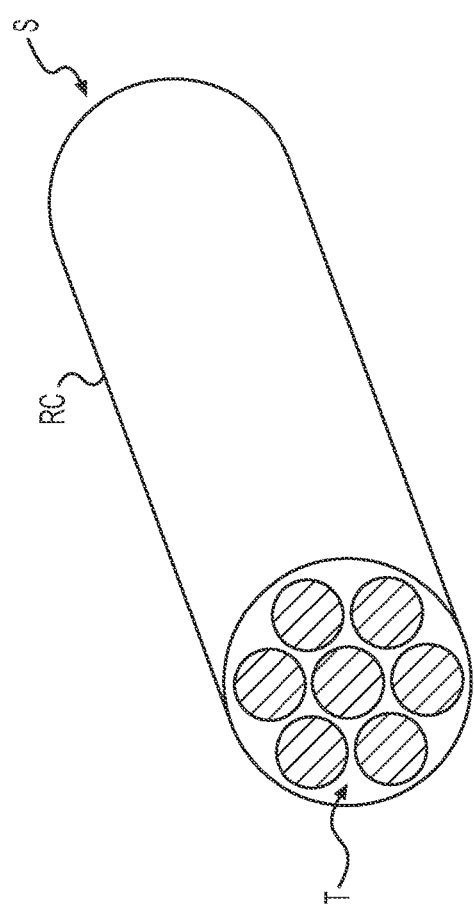
FIG. 1 is a perspective view of a wave generator used in the prior art.
Figure 2:
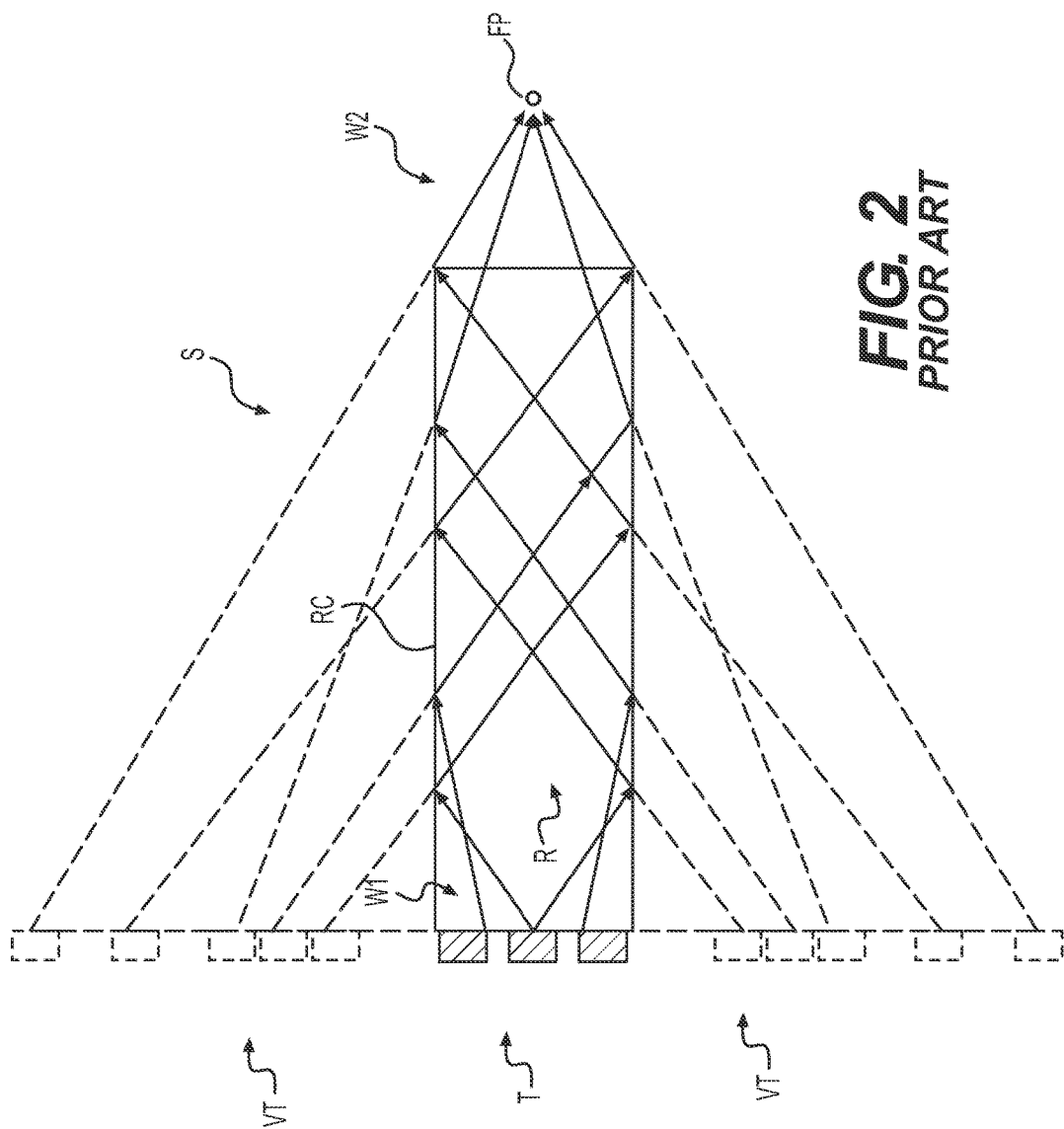
FIG. 2 is an illustration of reverberations inside the wave generator of FIG. 1.
Figure 3A:
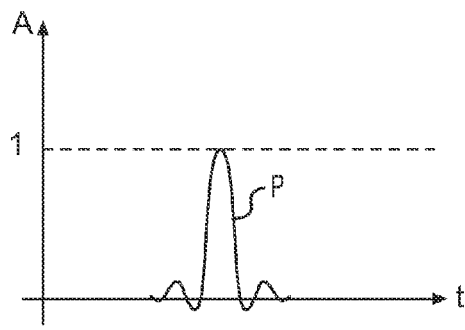
FIG. 3A is a graph of a pulse P (amplitude A vs. time t)
Figure 3D:
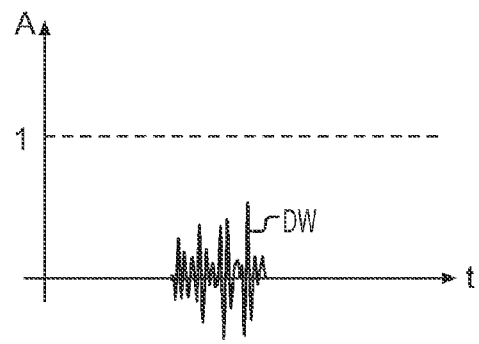
FIG. 3D is a graph of a dispersed wave DW (amplitude A vs. time t)
Figure 3B:
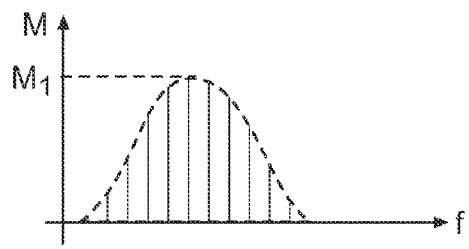
FIG. 3B is a graph of frequency components of the pulse P of FIG. 3A (magnitude M vs. frequency f)
Figure 3E:
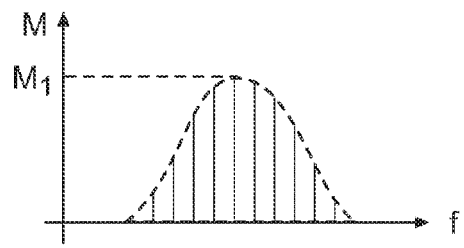
FIG. 3E is a graph of frequency components of the dispersed wave DW of FIG. 3D (magnitude M vs. frequency f)
Figure 3C:
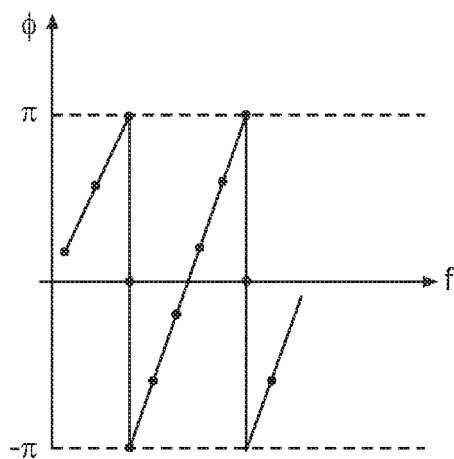
FIG. 3C is a graph of phases of the frequency components of the pulse P of FIG. 3A (phase $\phi$ vs. frequency f)
Figure 3F:
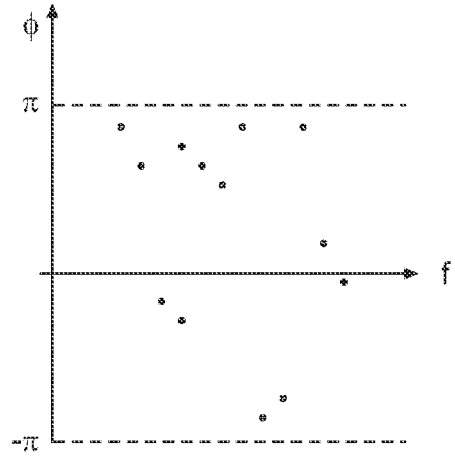
FIG. 3F is a graph of phases of the frequency components of the dispersed wave DW of FIG. 3D (phase $\phi$ vs. frequency f)
Figure 4:
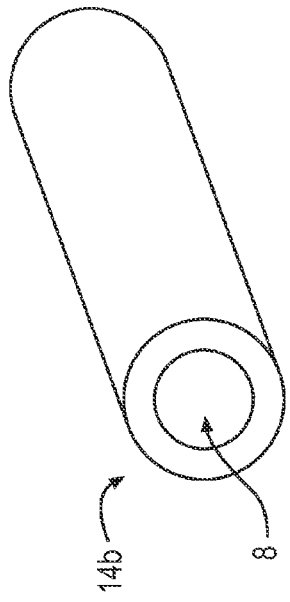
FIG. 4 is a wave emitter according to a first embodiment of the invention.

Referring to FIG. 4, a first embodiment of a wave emitter 10 will be described. The wave emitter 10 has a waveguide 14 and a single transducer 12 disposed at a first end 15 of the waveguide 14. A second end 16 of the waveguide 14 is free. When in operation, the second 16 is put into contact with a medium 104 in which the wave emitter 10 emits mechanical waves. The medium 104 and a method for generating mechanical waves will be described below.

The transducer 12 is fixedly disposed to the first end 15 by two screws (not shown) which exert pressure to retain the transducer 12 on the waveguide 14. It is contemplated that other ways to affix the transducer 12 to the waveguide 14 could be used. For example, the transducer 12 could be glued to the first end 15 of the waveguide. It is also contemplated that a gel (similar to the ones used in ultrasound imaging) could be disposed between the transducer 12 and the waveguide 14 to enhance energy transmission between the transducer 12 and the waveguide 14. The single transducer 12 is one example of source that could be used to generate mechanical waves into the waveguide 14.

Figure 5:
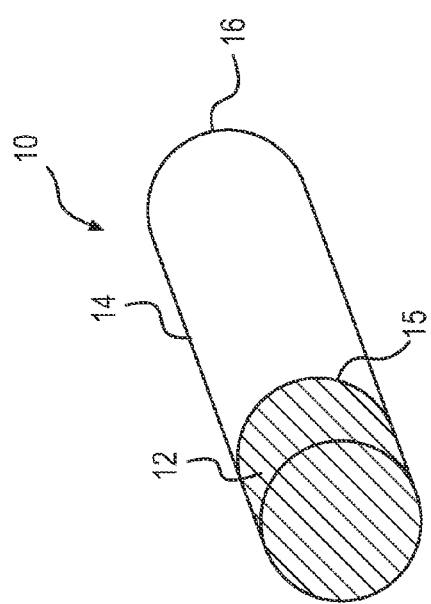
FIG. 5 is an embodiment of a waveguide for the wave emitter of FIG. 4.
Figure 6:
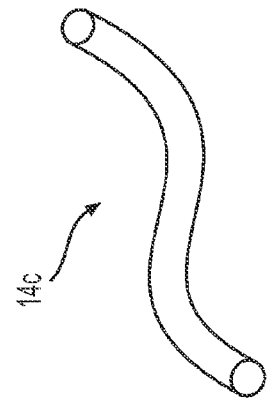
FIG. 6 is yet another embodiment of a waveguide for the emitter of FIG. 4.

The waveguide 14 is an elongated rod of circular cross-section. It is contemplated that a waveguide 14 could have a cross-section different from circular. As shown in FIG. 5, the waveguide 14 could be embodied as a waveguide 14a having a C-shape, and as shown in FIG. 6, the waveguide 14 could also be embodied as a waveguide 14b being hollow and having a hole 8 along its length. It is also contemplated that the waveguide 14 could be a combination of the waveguides 14a and 14b, and could have a C-shape and one or more hole 8 with same or different shape and sizes. It is also contemplated that the waveguide 14 could have yet different shapes of cross-section.

The waveguide 14 has a constant cross-section. It is contemplated that the waveguide 14 could not have a constant cross-section. For example, the waveguide 14 could have one end squared and another end circular and could transition smoothly between the two along its length. In another example, the waveguide is tapered.

The waveguide 14 has an aspect ratio of 40. It is contemplated that the aspect ratio of the waveguide 14 could range between 10 and 1000. A length of the waveguide 14 is 1000 mm, and a cross-section area is 25 mm (area: 490 mm$^2$). The length of the waveguide 14 is preferably chosen, on one end to accommodate the fact that the longer the waveguide 14, the more dispersed a mechanical wave will be (and therefore the higher the gain) and on the other end, to accommodate the fact that the longer the waveguide 14, the more attenuated the mechanical wave will be after propagation through the waveguide 14. It is contemplated that the waveguide 14 could have other dimensions. For example, the length of the waveguide 14 could be between 200 mm and 1500 mm, and the diameter could be between 1 mm and 50 mm.

Figure 7:
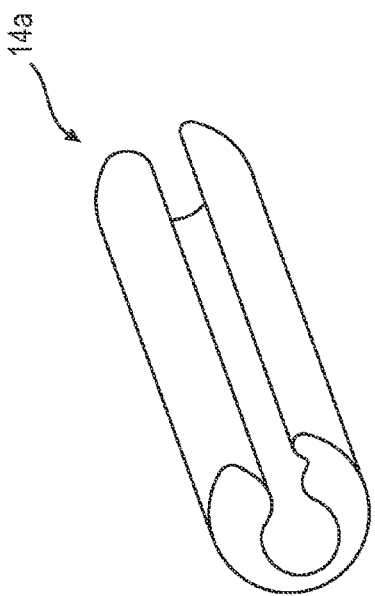
FIG. 7 is another embodiment of a waveguide for the wave emitter of FIG. 4.

The waveguide 14 is straight and inflexible. It is contemplated that the waveguide 14 could have some curvature. For example, a radius of curvature of the waveguide 14 could be one order of magnitude greater than a wavelength of a signal propagating through waveguide 14. As shown in FIG. 7, the waveguide 14 could be embodied as a waveguide 14C that is flexible. The flexible waveguide 14C could have a size and mechanical compliance adapted to allow insertion of the waveguide 14C in place where access is restricted.

The waveguide 14 is made of aluminum 6061-T6. It is contemplated that the waveguide 14 could be made of a different type of aluminum or a different material. It is also contemplated that the waveguide 14 could be made of an alloy of materials. For example the waveguide 14 could be made of aluminum, magnesium, stainless steel, titanium, etc. It is also contemplated that the waveguide 14 could be formed of two or more adjacently arranged waveguides. For example the waveguide 14 could be made of two concentrically arranged waveguides, each waveguide being made of a different material. The waveguide 14 is dispersive within a bandwidth of the transducer 12. The waveguide 14 also has a low attenuation coefficient around the central frequency of the transducer 12 for maximizing amplification gain.

The transducer 12 is a single gas matrix piezoelectric of The Ultran Group model GWC-D28-10. The transducer 12 has a diameter of 25 mm and is sized to cover an entirety of the first end 15 of the waveguide 14. It is contemplated that the transducer 12 could be bigger or smaller than the first end 15. When the transducer 12 is of the size or bigger than the cross-section of the waveguide 14, a planar wave can be generated. When the transducer 12 is smaller than the cross-section of the waveguide 14 multiple reflections at walls of the waveguide 14 may deform the planar wave as it travels the waveguide 14. The planar waves are generally unfocused and excite one or more longitudinal modes of the waveguide 14. It is contemplated that the mechanical waves could not be planar, could not be unfocused, and could excite modes other than longitudinal modes.

The transducer 12 is disposed at the first end 15 perpendicularly to a longitudinal direction of the waveguide 14. It is contemplated that the transducer 12 could be positioned at the first end 15 not perpendicularly to the longitudinal direction of the waveguide 14. It is contemplated that some reverberations could occur when the transducer 12 is not disposed perpendicularly to the longitudinal direction of the waveguide 14.

The transducer 12 has a central frequency of 600 kHz. It is contemplated that the transducer 12 could have a central frequency different from 600 kHz. The transducer's 12 central frequency is preferably chosen in accordance with the dispersive properties of the waveguide 14. In the present case, a central frequency of 600 kHz is desired because the waveguide 14 is made of aluminum and is dispersive within a range around 600 kHz for the dimensions of the waveguide 14 recited above. A bandwidth of the transducer 12 is from 300 kHz to 900 KHz. It is contemplated that the transducer 12 could have a different bandwidth.

Figure 8:
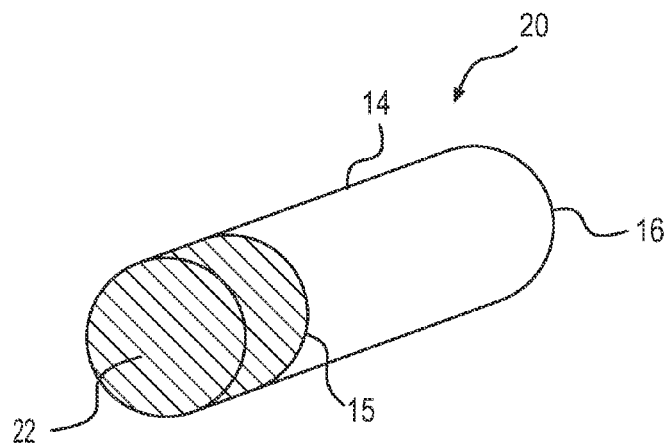
FIG. 8 is a wave emitter according to a second embodiment of the invention.

Referring now to FIG. 8, a second embodiment of a wave emitter 20 will now be described. The wave emitter 20 is similar to the wave emitter 10 but features a bi-directional transducer 22 in place of the unidirectional transducer 12. Elements of the wave emitter 20 common to the wave emitter 10 will have same reference numerals, and will not be described in detail herein again.

The bi-directional transducer 22 can convert electric signals into mechanical waves and reversely, mechanical waves into electrical signals. The bi-directional transducer 22 enables the wave emitter 20 to detect mechanical waves in a medium 104 (shown in FIG. 11) in addition to emitting mechanical waves in the medium 104. It is contemplated that a transducer assembly could replace the bi-directional transducer 22. The transducer assembly could be formed by the association of two transducers, the assembly covering the first end 15 of the waveguide 14. The two transducers could be disposed adjacent to each other or concentrically arranged. One of the two transducers could be used to emit mechanical waves, and the other to receive mechanical waves.

Figure 9:
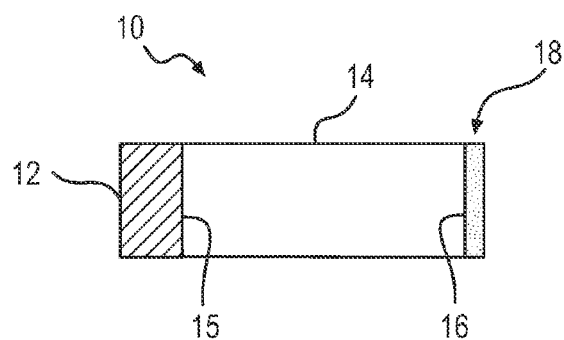
FIG. 9 is the wave emitter of FIG. 4 with an acoustic impedance coupler.

An acoustic impedance coupler 18 (shown in FIG. 9) can be coupled to any of the wave emitters 10 and 20 for increasing energy transmission of the mechanical wave between the second end 16 of the waveguide 14, and the medium 104. The acoustic impedance coupler 18 includes a layer of glass and a layer of epoxy between the glass and the second end 16 of the waveguide 14. The epoxy is used to glue the glass to the waveguide 14. Each of the layers of epoxy and glass is disk shaped to match the circular cross-section of the waveguide 14. The layer of epoxy has a thickness of 730 μm, and the layer of glass has a thickness of 300 μm. The acoustic impedance coupler 18 has an acoustic impedance intermediate to an acoustic impedance of the waveguide 14 and to an acoustic impedance of the medium 104. It is contemplated that the acoustic impedance coupler 18 could be embodied as a structure having different shape or material, or be even a gel or a softer material. It is also contemplated that the acoustic impedance coupler 18 could include a plurality of layers of glass and epoxy.

Figure 10:
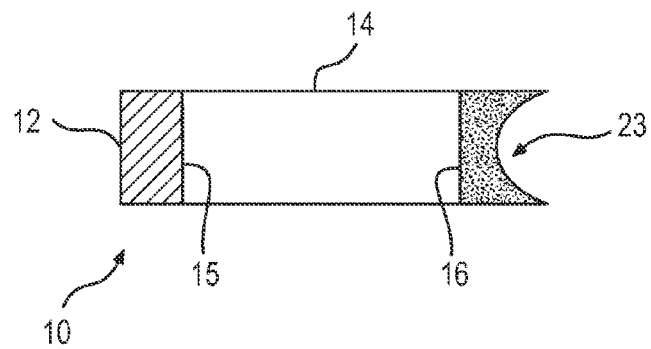
FIG. 10 is the wave emitter of FIG. 4 with an acoustic lens.

An acoustic lens 23 (shown in FIG. 10) can be disposed at the second end 16 of the waveguide 14 of any of the wave emitters 10 and 20, to geometrically focus the mechanical waves emitted into the medium 104. It is also contemplated that the wave emitters 10 and 20 could have the acoustic lens 23 and the acoustic impedance coupler 18 disposed is series at the second end 16 of the waveguide 14. It is also contemplated that the acoustic lens 23 could not be used for focusing the mechanical waves emitted into the medium 104. For example, the wave emitters 10 and 20 could exploit diffraction effects at the second end 16 of the waveguide 14 to focus energy at a predetermined spatial location within the medium 104. Diffraction patterns are dependent on the shape and size of the second end as well as on a wavelength of the desired output wave. In other example, the second end 16 of the waveguide 14 could be shaped so as to geometrically focus the mechanical waves.

Figure 11:
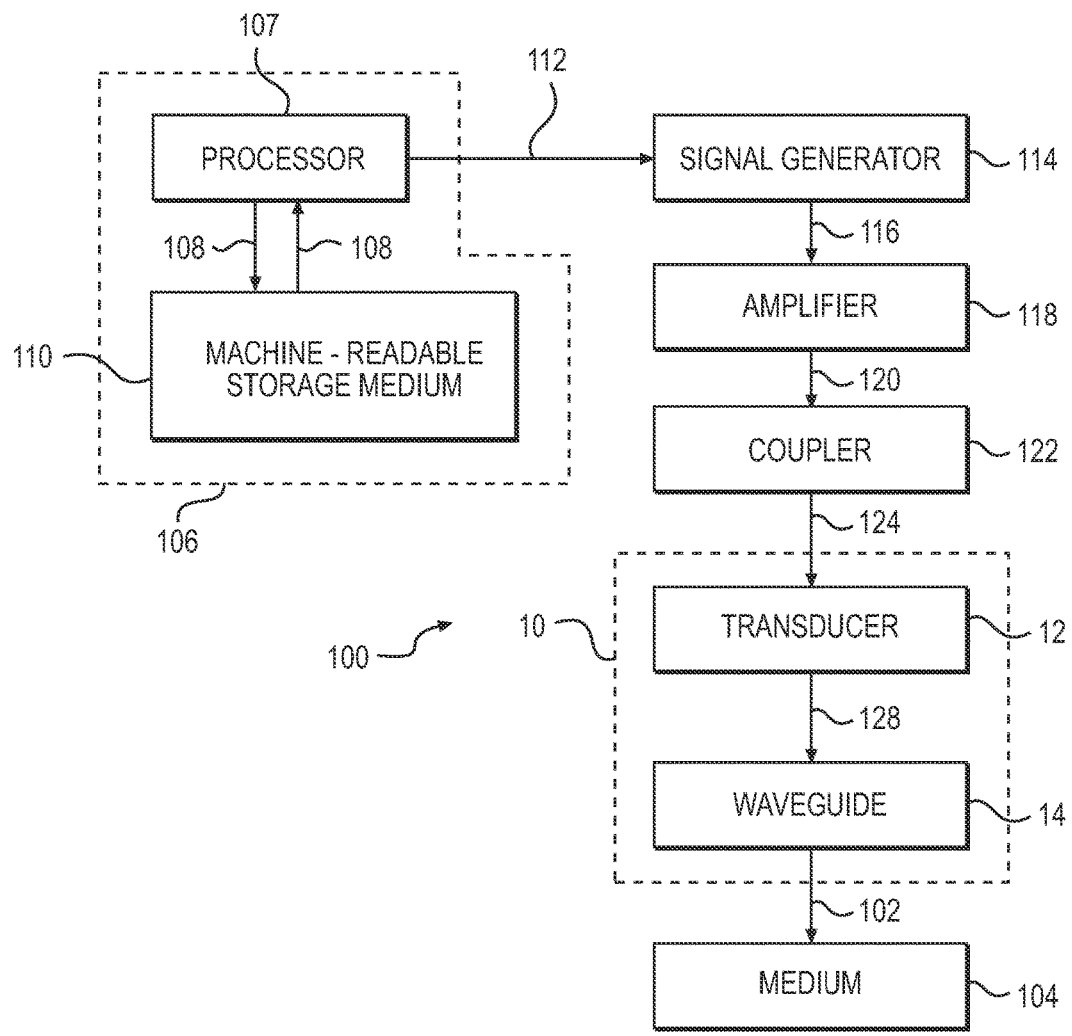
FIG. 11 is a schematic representation of a wave generator for the wave emitter of FIG. 4.

Referring to FIG. 11, a wave generator 100 will now be described. The wave generator 100 is a system powering the wave emitter 10 and used to program the wave emitter 10 to generate desired mechanical waves.

The wave emitter 10 is powered by a signal generator 114, which is programmable by a computer 106. The signal generator 114 is a National Instruments, PXI 5412 (14-Bit 100 MS/s). The computer 106 is a general purpose computer well known in the art. It is contemplated that the computer 106 could be another type of computing interface. It is contemplated that the signal generator 114 could be different. The computer 106 has a processor 107 in communication (data 108) with a machine-readable storage medium 110. The machine-readable storage medium 110 is used to store the data 108, which are digitized input signals corresponding to mechanical input waves 128. The computer 106 constitutes an interface used by a user to program an input signal 112 that will lead to the generation of one or more mechanical input waves 128.

The signal generator 114 transforms the input signal 112 into a low voltage signal 116. The low voltage signal 116 is transformed into a higher voltage signal 120 by an amplifier 118. The amplifier 118 is a RITEC, GA-2500A (400 Watts). It is contemplated that the amplifier 118 could be different. The higher voltage signal 120 goes through a coupler 122 which optimizes power transfer between the amplifier 118 and the wave emitter 10 by coupling electric impedances of the amplifier 118 and the wave emitter 10. It is contemplated that the amplifier 118 could be omitted. After passage through the coupler 122, the higher voltage signal 120 becomes input voltage signal 124 to the wave emitter 10. It is contemplated that the coupler 122 could be omitted.

The transducer 12 converts the input voltage signal 124 into the mechanical input wave 128, and the waveguide 14 propagates the mechanical input wave 128 towards the second end 16 of the waveguide 14 which is being put in contact with the medium 104 for generating mechanical waves 102 in the medium 104. The medium 104 is degassed tap water at room temperature. It is contemplated that the medium 104 could be different. The waveguide 14 being dispersive, the mechanical input wave 128 is distorted into a mechanical output wave 102 by the time the mechanical input wave 128 has reached the second end 16. Some component waves of the mechanical input wave 128 travel faster than others and can reach the second end 16 at the same time as the slower component waves. When the slower and faster components waves reach simultaneously the second end 16 an interaction occurs to form the mechanical output wave 102. The mechanical output wave 102 is a recombination of the mechanical input wave 128. At the second end 16 of the waveguide 14, the mechanical output wave 102 is emitted into the medium 104.

To use the wave generator 100, the user starts with determining the desired mechanical output wave 102 that he/she wishes to emit in the medium 104. The user uses the computer 106 to determine the input signal 112 input to the signal generator 114 that ultimately will lead to the mechanical output wave 102 after conversion by the transducer 12 and propagation through the dispersive waveguide 14. A method for generating the mechanical output waves 102 will be described below.

The input signal 112 is calculated taking into consideration the dispersive properties of the waveguide 14 and in some cases taking into consideration the physical properties of the medium 104. The dispersive properties of the waveguide 14 and the physical properties of the medium 104 are determined in a prior calibration step typically done only once. The waveguide 14 is calibrated using the impulse response method. It is contemplated that other methods well known in the art could be used to calibrate the waveguide 14. For example, time reversal mirror, inverse filter, or analytical calculation of dispersion curves could be used. In the impulse response method, a known pulse is sent by the transducer 12 into the waveguide 14, and after traveling through the waveguide 14 and being deformed due to the dispersive properties of the waveguide 14, the pulse propagates in the medium 104 until reaching a hydrophone (not shown) priory placed in front of the waveguide 14. An advantage of the impulse response calibration method is that it allows to take into consideration the characteristics of the medium 104 itself. It is possible that the choice of medium 104 influences a shape of the mechanical output waves 102, after having been generated at the second end 16, when the mechanical output waves 102 enter the medium 104. Therefore, it is preferable that the calibration takes into consideration the medium 104. It is contemplated that the medium 104 could be calibration in a separate calibration step. It is also contemplated that the physical properties of the medium 104 could not be calibrated. The hydrophone is a Müller-Platte Needleprobe 100-100-1 with a sensitive diameter inferior to 0.5 mm. It is contemplated that the hydrophone could be different. The hydrophone records the emitted wave which is used along with the impulse to characterize a frequency response function of the wave emitter 10. The frequency response function is a key of the system (wave emitter 10) which once known allows to determine how any wave will be modified into, after propagation in the dispersive waveguide 14. It is contemplated that if the transducer 12 were bi-directional, it could be possible to use, instead of the hydrophone, a reflection of the impulse itself at the second end 16 of the waveguide 14 in order to determine the frequency response function of the wave emitter 10.

Figure 12:
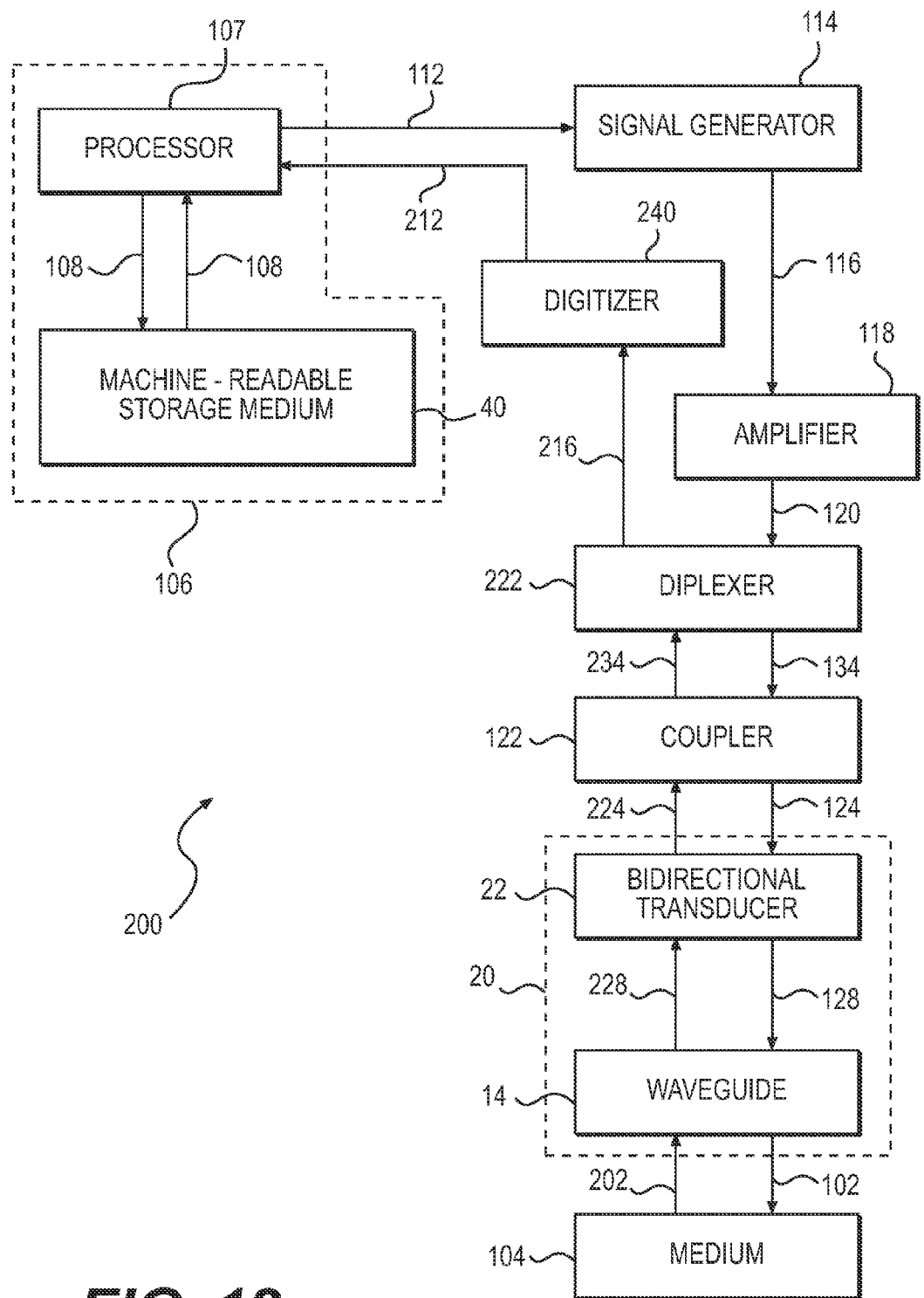
FIG. 12 is a schematic representation of a wave generator for the wave emitter of FIG. 7.

Referring now to FIG. 12, a wave generator 200 will now be described. The wave generator 200 is a system powering the wave emitter 20 used to generate the desired mechanical output waves 102 and further to record information coming from the medium 104 for the purpose of, for example, locating a non-homogeneity in the medium 104. The wave generator 200 is similar to the wave generator 100, but features a diplexer 222 and a digitizer 240. Elements of the wave generator 200 common to the wave generator 100 will have same reference numerals, and will not be described herein again.

The diplexer 222 is located between the amplifier 118 and the coupler 122. The diplexer 222 acts as a switch to separate electric signals 124 incoming and outgoing the bi-directional transducer 22. For example, the diplexer 222 separates signals 234 incoming from the medium 104 through the waveguide 14 from signals 134 incoming from the signal generator 114. The diplexer 222 is only one example of a switch. The digitizer 240 transforms a signal 216 outgoing from the diplexer 222 into a signal 212 readable by the computer 106. The bi-directional transducer 22 converts the voltage signal 124 into the corresponding mechanical input wave 128, and reversely converts a mechanical wave 228 coming from the waveguide 14 (reverse direction mechanical wave) into a corresponding electric signal 224.

Emission of mechanical waves by the wave generator 200 is similar to the one described below for the wave generator 100, except that the higher voltage signal 120 goes through the diplexer 222 and the coupler 122 before entering the wave emitter 20 without being noticeably deformed.

Reception of mechanical waves by the wave generator 200 starts with the waveguide 14 receiving a mechanical wave 202 (e.g. perturbation) from the medium 104 at the second end 16. The mechanical wave 202 could be emitted from a source in the medium 104 or reflected by a non-homogeneity in the medium 104. The mechanical wave 202 propagates through the waveguide 14 toward the bi-directional transducer 22. When the mechanical wave 202 reaches the bi-directional transducer 22, the mechanical wave 202 has been transformed into the mechanical wave 228 which is a dispersed version of the mechanical wave 202. The bi-directional transducer 22 converts the mechanical wave 228 into a corresponding electric signal 224. The electric signal 224 goes through the coupler 122, becomes signal 234, goes through the diplexer 222 becomes the signal 216, before reaching the digitizer 240, and being transformed into the signal 212 readable by the computer 106.

As mentioned above, the wave emitter 20 can be used as a location device for a non-homogeneity. The calibration of the wave emitter 20 can be done in a unique calibration step, analytically or experimentally. The calibration of the wave emitter 20 is similar to the calibration for the wave emitter 10 described above. A method for locating a non-homogeneity in the medium 104 starts with the wave emitter 200 emitting a pulse. Then, the pulse is reflected by the non-homogeneity and reaches back the wave emitter 20 (with some distortion due to propagation in the medium 104). Dispersion in the waveguide 14 is taken into consideration by the prior calibration of the wave emitter 20. The reflected mechanical wave from the non-homogeneity is compared with the original pulse sent toward the non-homogeneity to determine a distance between the second end 16 of the waveguide 14 and the non-homogeneity. Comparison can be performed by the computer 106. It is also possible to exploit the waves reflected by the non-homogeneity to characterize heterogeneities in the medium 104.

Figure 13:
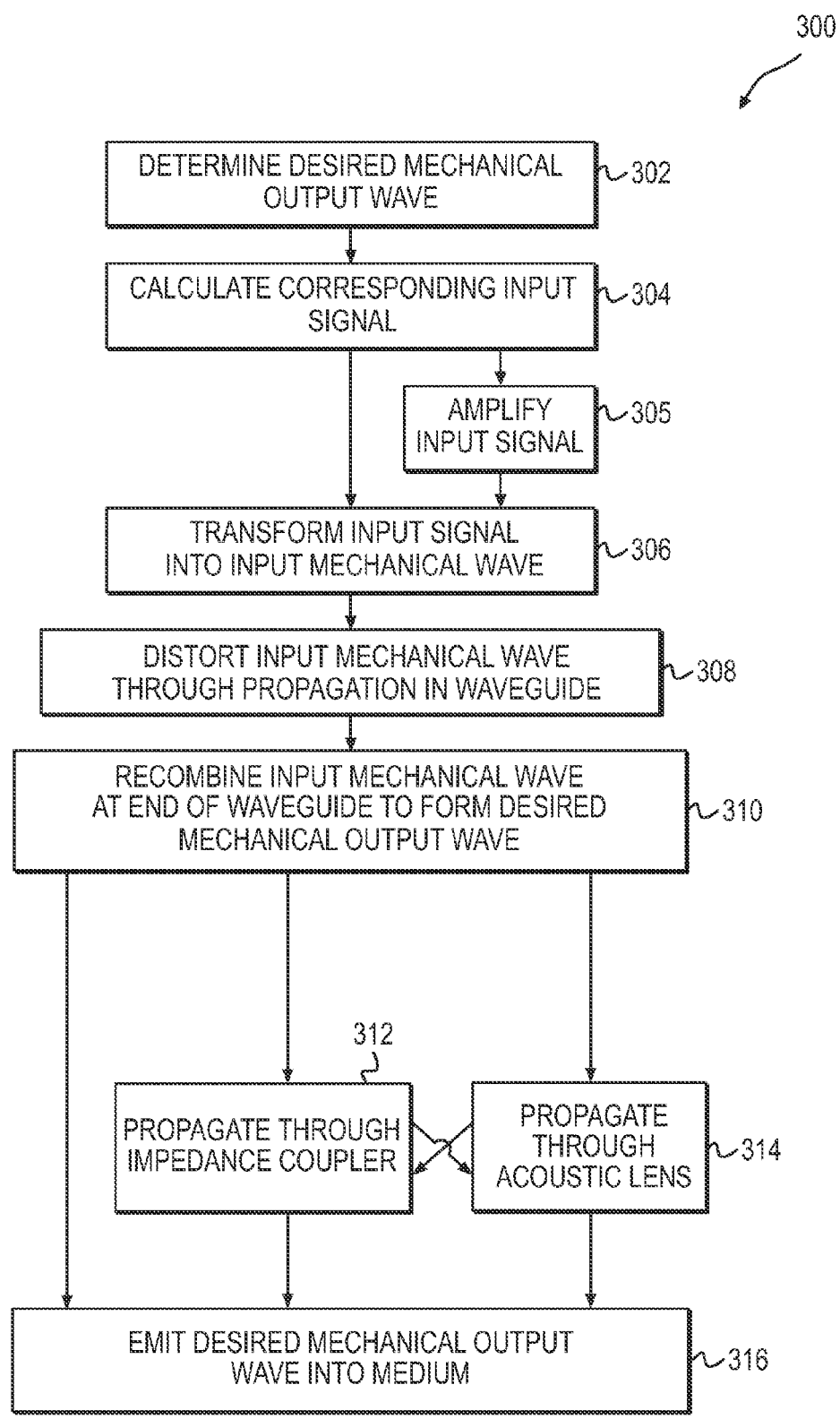
FIG. 13 is a flow chart illustrating a method for emitting a desired mechanical output wave.

Referring now to FIG. 13, a method 300 for generating a desired mechanical wave by exploiting waveguide dispersion of the wave emitter 10 in the wave generator 100 will now be described. The method 300 will be described assuming the wave emitter 10 has been priory calibrated and the dispersive properties of the waveguide 14 (and optionally the physical properties of the medium 104) are known, as described above. It is contemplated that the method 300 could be used for generating a desired mechanical wave by exploiting waveguide dispersion of the wave emitter 20 in the wave generator 200.

The method 300 starts at step 302, with the user determining the desired mechanical output wave 102. As described above, the desired mechanical output wave 102 has at least two component waves having relative phases between them. Each component wave has (among other characteristics) an associated frequency and an associated mode within the predetermined range of frequencies and modes for which the waveguide 14 is dispersive.

At step 304, the input signal 112 is calculated by the computer 106. The input signal 112 corresponds to the mechanical input wave 128 produced by the transducer 12, which once distorted by the dispersive waveguide 14 will recombine into the desired mechanical output wave 102. As mentioned above, the input signal 112 is calculated taking into account the dispersive relations of the waveguide 14, so as to compensate at the end 16 of the waveguide 14 for the relative phase shifts introduced by the waveguide 14 as the components waves of the mechanical input wave 128 travel through it.

From step 304 the method 300 can go either through step 305, or directly to step 306. At step 305, the input signal 112 is amplified. One way to amplify the input signal 112 is to saturate it before amplifying it. To do so, a magnitude of the input signal 112 for the different frequencies composing it, is fixed to a limit value, and consequently amplified. Saturating and amplifying the input signal 112 allows to amplify without affecting relative phases. It is contemplated that one could amplify and then saturate the input signal 112. It is contemplated that the saturation and amplification could be done differently. An example of amplification by saturation is given below.

At step 306, the input signal 112 is transformed by the transducer 12 into the mechanical input wave 128. The mechanical input wave 128 travels through the waveguide 14 and gets distorted due to the dispersive properties of the waveguide 14.

A step 310, the desired mechanical output wave 102 is generated from a recombination of the mechanical input wave 128 at the second end 16. Once the desired mechanical output wave 102 is generated, it is emitted into the medium 104 at step 310. If at step 312, the wave emitter 10 is coupled to the acoustic impedance coupler 18, the desired mechanical output wave 102 propagates through the acoustic impedance coupler 18 before reaching the medium 104. If at step 314 the wave emitter 10 is coupled to the acoustic lens 23, the desired mechanical output wave 102 propagates through the acoustics lens 23 before reaching the medium 104 at step 314. The wave emitter 10 could also be coupled to the acoustic lens 23 and the acoustic impedance coupler 18.

Figure 14:
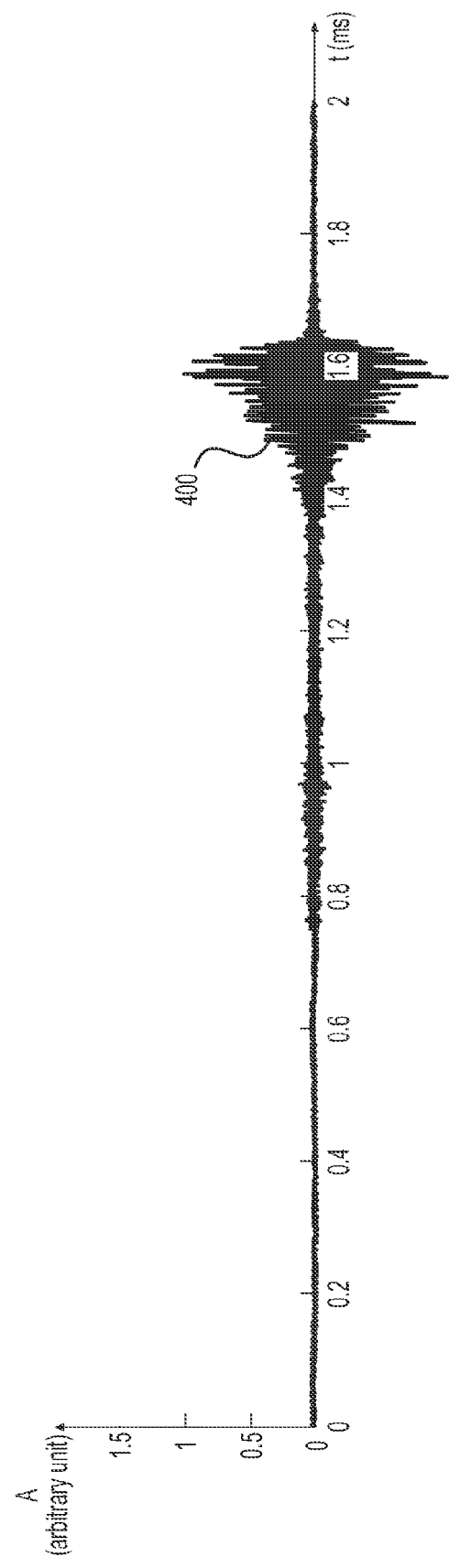
FIG. 14 is a graph of amplitude A vs. time t of an example of a mechanical input wave.
Figure 15:
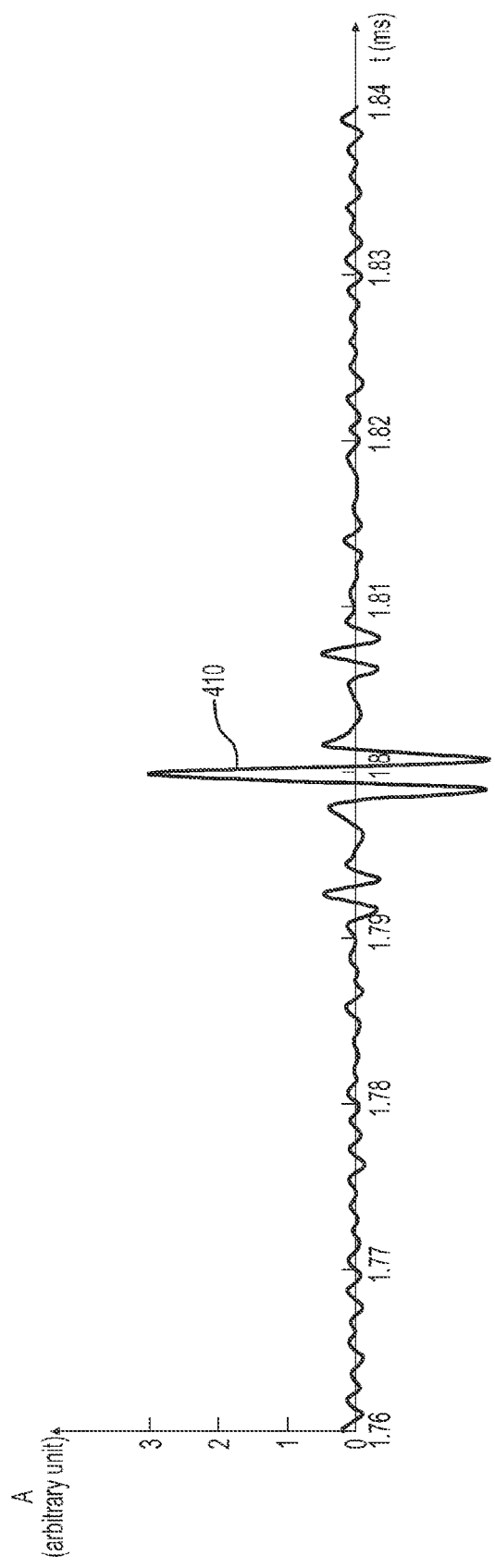
FIG. 15 is a graph of an example of a desired mechanical output wave (amplitude A vs. time t)
Figure 16:
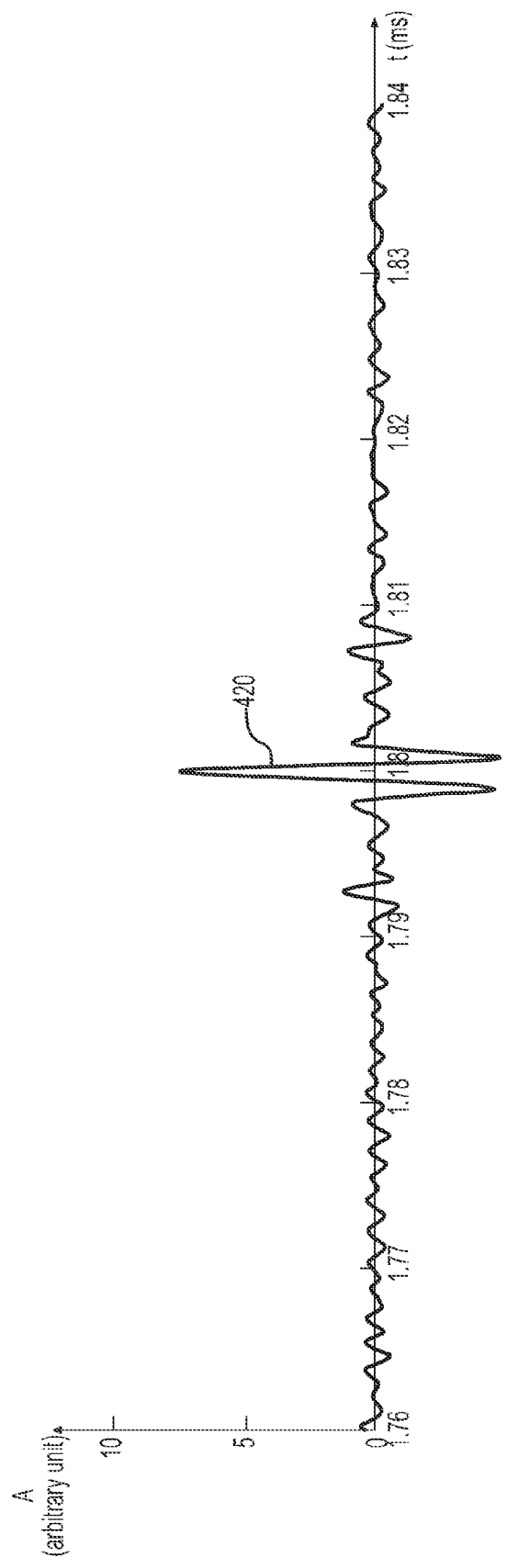
FIG. 16 is a graph of another example of a desired mechanical output wave (amplitude A vs. time t)
Figure 17:
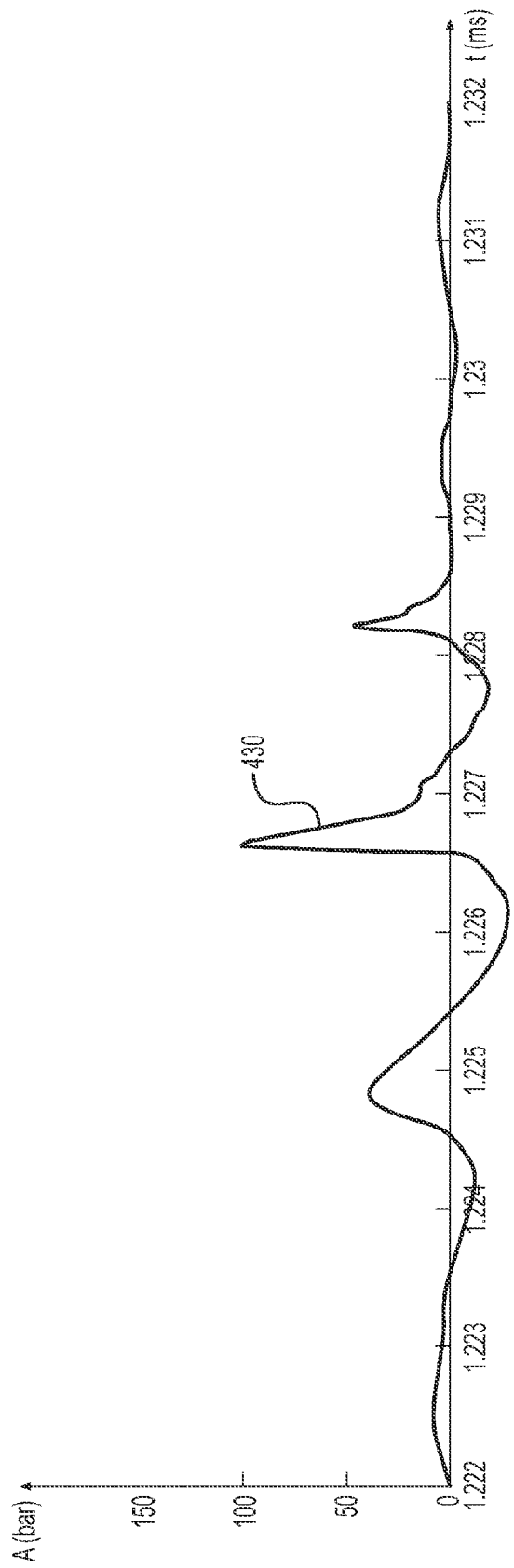
FIG. 17 is a graph of the desired mechanical output wave of FIG. 15 (amplitude A vs. time t) recorded at some distance from the waveguide.

Turning now to FIGS. 14 to 17, an example of mechanical input wave 128 and a resulting desired mechanical output wave 102 will be described. In the experiment leading to the results shown in FIGS. 14 to 17, the wave emitter 10 is connected to the impedance acoustic coupler 18 but has no acoustic lens 23 attached to it. As mentioned earlier, the medium 104 is degassed tap water at room temperature. The wave emitter 10 is positioned so as to have the second end 16 in contact with the medium 104. In this experiment, the user desires to emit a pulse of a normalized amplitude of 3 and a desired time signature of 1.67 µs. It is contemplated that the experiment could be performed for generating a pulse other than the one above. It is also contemplated that the experiment could be performed for generating mechanical waves other than a pulse. The user uses the computer 106 to determine a mechanical input wave 400 that needs to be generated by the transducer 12 in order to generate at the second end 16 of the waveguide 14, the desired pulse. FIG. 14 shows the mechanical input wave 400 as generated by the transducer 12. As can be noticed, the wave 400 is characterized by a time signature of 0.2 ms and an amplitude of 1 (FIG. 14 showing the amplitude normalized). As shown in FIG. 15, a pulse 410 characterized by a time signature of approximately 1.67 µs and an amplitude of 3 (FIG. 15 showing the amplitude normalized) is recorded at the second end 16 of the waveguide 14. It can be seen that, the wave generator 10 has passively compressed in time and has amplified the wave 400 to form the pulse 410. The gain is 3 and the temporal compression is of a factor of 120. As mentioned above, the user can also saturate the signal leading to the generation of the mechanical input wave 400, so as to amplify even further the amplitude of the desired pulse 410. As shown in FIG. 16, when recorded at the second end 16 of the waveguide 14 is a pulse 420 having the same time signature as the pulse 410, but having an amplitude of 8 (FIG. 16 showing the amplitude normalized). Saturation did not affect the time signature, and has increased the amplitude by about 2.7 times compared to the same experiment without saturation. With saturation the overall gain of this experiment is 8. Once the pulses 410 and 420 are emitted in the medium 104, non-linear effects of the medium 104 distort the pulses 401, 402 as they travel through it. As shown in FIG. 17 for the pulse 410, at 70 mm along a longitudinal axis of the waveguide 14, the pulse 410 has becomes a shockwave 430. The shockwave 430 is characterized by a time signature of less than 1 µs and an amplitude of 100 bars. This amplitude of the shockwave 430 is 20 times more than a wave that would be created by the same transducer 12 (without waveguide 14), driven by the same electrical power and emitting in the same medium 104 (water).

Modifications and improvements to the above-described embodiments of the present invention may become apparent to those skilled in the art. The foregoing description is intended to be exemplary rather than limiting. The scope of the present invention is therefore intended to be limited solely by the scope of the appended claims.

What is claimed is:

1. A wave generator for emitting a desired mechanical output wave into a medium, the wave generator comprising:
   a wave emitter including:
   an elongated dispersive waveguide having a first end and a second end, when in operation the second end being at least partially in contact with the medium; and
   a source operatively connected to the first end of the dispersive waveguide covering at least partially a surface area of the first end, the source being operative to generate a mechanical input wave in the dispersive waveguide based on electrical signals input to the source;
   a signal generator in operative connection with the source, the signal generator being operative to create the electrical signals convertible by the source into the mechanical input wave in the dispersive waveguide; and
   a computer in operative connection with the signal generator, the computer having a processor and a machine-readable storage medium, the machine-readable storage medium containing instructions that when executed by the processor causes the signal generator to create electrical signals convertible by the source into the mechanical input wave,
   the mechanical input wave having at least two component waves, each of the at least two component waves having a unique predetermined propagation velocity through the dispersive waveguide,
   the at least two component waves having one of different predetermined propagation velocities through the dispersive waveguide and a first relative phase shift being determined so as to be become, at the second end of the dispersive waveguide, a second relative phase shift different from the first relative phase shift owing to the predetermined propagation velocities through the dispersive waveguide of the at least two component waves,
   wherein, if the at least two component waves have the different predetermined propagation velocities through the dispersive waveguide, the mechanical input wave is constructed (i) independently of data related to a mechanical wave received from a source in the medium and (ii) taking into account the different predetermined propagation velocities of the at least two component waves so that the at least two component waves combine at least partially with each other at the second end of the dispersive waveguide to form the desired mechanical output wave emitted into the medium.

2. The wave generator of claim 1, wherein the mechanical input wave has a first duration in time, the desired mechanical output wave has a second duration in time, and the first duration in time is longer than the second duration in time.

3. The wave generator of claim 1, wherein the mechanical input wave has a first amplitude, the desired mechanical output wave has a second amplitude, and the second amplitude is greater than the first amplitude.

4. The wave generator of claim 1, wherein the at least two component waves have different associated frequencies, and the at least two component waves have a same associated mode of the waveguide.

5. The wave generator of claim 4, wherein the same associated mode is a single mode of the waveguide.

6. The wave generator of claim 5, wherein the single mode is a fundamental longitudinal mode of the waveguide.

7. The wave generator of claim 1, wherein the at least two component waves have each an associated frequency and an associated mode of the waveguide, the at least two component waves have different associated modes, and the at least two component waves have a same associated frequency.

8. The wave generator of claim 1, wherein the source operatively connected to the first end of the dispersive waveguide is a transducer.

9. The wave generator of claim 1, wherein the source covers at least an entirety of the surface area of the first end of the dispersive waveguide.

10. The wave generator of claim 1, further comprising at least one of an acoustic impedance coupler and an acoustic lens operatively connected to the second end of the dispersive waveguide.

11. The wave generator of claim 1, wherein the desired mechanical output wave is focused.

12. The wave generator of claim 1,
wherein the source is a bi-directional source, and is further operative to generate output electrical signals from a reverse direction mechanical wave, the reverse direction mechanical wave propagating through the dispersive waveguide from the second end to the first end of the dispersive waveguide; and
the wave generator further comprising:
a switch in operative connection with the bi-directional source, the switch being operative to separate input electric signals to be input to the bidirectional source from output electric signals out from the bi-directional source; and
a digitizer in operative connection with the switch and with the computer, the digitizer being operative to digitize the output electrical signals for use by the computer.

* * * * *